US012642680B2

(12) United States Patent
    Greenberg

(10) Patent No.: US 12,642,680 B2
(45) Date of Patent: Jun. 2, 2026

(54) ORTHOSIS

(71) Applicant: Shai Greenberg, Herzliya (IL)

(72) Inventor: Shai Greenberg, Herzliya (IL)

( * ) Notice: Subject to any disclaimer, the term of this patent is extended or adjusted under 35 U.S.C. 154(b) by 49 days.

(21) Appl. No.: 18/719,337

(22) PCT Filed: Dec. 15, 2022

(86) PCT No.: PCT/IL2022/051339
    § 371 (c)(1),
    (2) Date: Jun. 13, 2024

(87) PCT Pub. No.: WO2023/112037
    PCT Pub. Date: Jun. 22, 2023

(65) Prior Publication Data
    US 2025/0057681 A1      Feb. 20, 2025

Related U.S. Application Data

(60) Provisional application No. 63/361,330, filed on Dec. 15, 2021.

(51) Int. Cl.
    *A61F 5/01*        (2006.01)
(52) U.S. Cl.
    CPC .... *A61F 5/0125* (2013.01); *A61F 2005/0155* (2013.01)
(58) Field of Classification Search
    CPC .................. A61F 5/0123; A61F 5/0125; A61F 2005/0132; A61F 2005/0137; A61F 2005/0139; A61F 2005/0155; A61F 2005/0158; A61F 2005/0174; A61F 2005/0179; A61F 2005/0197; A61F 5/01–34; A61H 1/02; A61H 1/0214; A61H 1/0237; A61H 1/024; A61H 1/0244; A61H 1/0274; A61H 1/0277; A61H 1/0281;
(Continued)

(56) References Cited

U.S. PATENT DOCUMENTS

2008/0200856 A1     8/2008  Cadichon
2013/0110020 A1*    5/2013  Ingimundarson ..... A61F 5/0123
                                                                 602/26
(Continued)

FOREIGN PATENT DOCUMENTS

EP          3090708        11/2016
WO        WO 95/35075      12/1995
WO      WO 2023/112037      6/2023

OTHER PUBLICATIONS

International Preliminary Report on Patentability Dated Jun. 27, 2024 From the International Bureau of WIPO Re. Application No. PCT/IL2022/051339. (6 Pages).
(Continued)

*Primary Examiner* — Rachael E Bredefeld
*Assistant Examiner* — Seth R. Brown

(57)                    ABSTRACT
A leg orthosis including a first brace attachable to a femoral portion of a leg and a second brace attachable to a tibial portion of said leg. The leg orthosis includes an articulation mechanism for enabling articulation of the leg orthosis and at least one force-applying mechanism for applying a pulling force to the second brace in a direction of the first brace, the force applied by the force-applying mechanism varies with an angle of articulation of the leg orthosis.

7 Claims, 7 Drawing Sheets

(58) Field of Classification Search
CPC ...... A61H 2201/1463; A61H 2201/149; A61H
2201/165
USPC ........................................ 602/16, 20, 23, 26
See application file for complete search history.

(56) References Cited

U.S. PATENT DOCUMENTS

| | | |
|---|---|---|
| 2013/0150761 A1 | 6/2013 | Romo et al. |
| 2014/0213948 A1 | 7/2014 | Romo et al. |
| 2015/0374530 A1 | 12/2015 | Bosshard et al. |
| 2016/0151189 A1* | 6/2016 | Romo ...................... A61H 3/00 602/16 |
| 2017/0071775 A1* | 3/2017 | Garrish ................. A61F 5/0102 |
| 2018/0280178 A1* | 10/2018 | Shimada ................ B25J 9/1045 |
| 2019/0053933 A1 | 2/2019 | Chetlapalli et al. |

OTHER PUBLICATIONS

International Search Report and the Written Opinion Dated Mar. 26, 2023 From the International Searching Authority Re. Application No. PCT/IL2022/051339 (11 Pages).
Supplementary European Search Report and the European Search Opinion Dated Oct. 24, 2025 From the European Patent Office Re. Application No. 22906861.4. (9 Pages).

* cited by examiner

10

ORTHOSIS

RELATED APPLICATIONS

This application is a National Phase of PCT Patent Application No. PCT/IL2022/051339 having International filing date of Dec. 15, 2022, which claims the benefit of priority under 35 USC § 119 (e) of U.S. Provisional Patent Application No. 63/361,330 filed on Dec. 15, 2021. The contents of the above applications are all incorporated by reference as if fully set forth herein in their entirety.

BACKGROUND

The present invention relates to an orthosis and to methods of using same for joint injury rehabilitation. Embodiments of the present invention relate to a leg orthosis that applies a pulling force of varying magnitude on a tibial component throughout flexion to thereby mimic the natural biomechanics of the knee.

Anterior cruciate ligament (ACL) rupture is the most common ligament injury in sport accounting for over 300,000 reconstruction surgeries in the United States each year.

The ACL is located between the femur and the tibia at the anterior portion of the knee. Its role is to stabilize the knee by preventing anterior translation of the tibia. Rupture of the ACL is most common with professional athletes and typically occurs when the knee is flexed at 25-30 degree and the femur internally rotates while the tibia externally rotates such that the ACL is placed under a high load or when the knee is extended at high speed and the femur moves backwards with respect to the tibia loading the ACL. Recent research has suggested that ACL Ruptures can also be caused by chronic strain on the ACL that produces microtears in the ligament and weakens its ability to produce passive force.

Surgical intervention is considered the best solution for ACL ruptures and is followed by a rehabilitation period of up to 1 year or more depending on the nature of injury. With professional athletes, such a long rehabilitation period can severely impact their professional career.

Exercise is considered the best approach for reducing the incidence of ACL rupture. Exercise is mainly focused on improving the Hamstring quadricep ratio (Ham/Q ratio) by strengthening the hamstring. During landing, as the knee starts to flex the quadricep muscle pulls the tibia anteriorly increasing the tension on the ACL. The hamstring works against the quadricep pulling the tibia in a posterior direction thereby decreasing the load on the ACL. That is why strengthening the hamstring can reduce the likelihood of ACL rupture.

Although ACL ruptures are very common to date there is no tool or device that can directly prevent such injury and/or substantially decrease the time needed for rehabilitation following surgery.

There is thus a need for a device that can be used in knee injury rehabilitation and in conditioning a knee in order to prevent injury or re-injury.

SUMMARY

According to one aspect of the present invention there is provided a leg orthosis comprising a first brace attachable to a femoral portion of a leg; a second brace attachable to a tibial portion of the leg; an articulation mechanism for enabling articulation of the leg orthosis; and a force-applying mechanism for applying a pulling force to the second brace in a direction of the first brace, wherein the force applied by the force-applying mechanism varies with an angle of articulation of the leg orthosis.

According to embodiments of the present invention the force is about 0 at full extension, linearly increases to a maximum of 600-2000 Newtons over a range of 0-15 degrees and decreases to a minimum of zero over a range of 30-90 degrees.

According to embodiments of the present invention the force applying mechanism includes a rotatable element for applying a pulling force on a strap or wire interconnecting the first brace and the second brace.

According to embodiments of the present invention the force applying mechanism further includes pulleys for carrying the strap or wire.

According to embodiments of the present invention the rotatable element includes cams and troughs for moving the pulleys radially in and out as the rotatable element is rotated.

According to embodiments of the present invention the force applying mechanism includes two rotatable elements and six pulleys and further wherein a first rotatable element moves a first set of three pulleys and a second rotatable element moves a second set of three pulleys.

According to embodiments of the present invention the strap or wire is connected to the first or the second brace via a spring.

According to embodiments of the present invention the force-applying mechanism is integrated into the articulation mechanism.

According to embodiments of the present invention the force applied by the force-applying mechanism is configured to mimic a pulling force of an ACL on the tibial portion.

According to embodiments of the present invention the pulleys are mounted within radially projecting slots.

According to embodiments of the present invention the force-applying mechanism includes a mechanism for setting a force applied at each degree range.

According to another aspect of the present invention there is provided method of treating or rehabilitating a knee injury comprising: fitting an orthosis having a first brace attachable to a femoral portion of a leg, a second brace attachable to a tibial portion of the leg and an articulation mechanism for enabling articulation of the leg orthosis on a leg of a subject; and using the orthosis to repeatedly apply a pulling force to the second brace in a direction of the first brace that varies with an angle of articulation of the leg orthosis thereby treating or rehabilitating the knee injury.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Figure 1A:
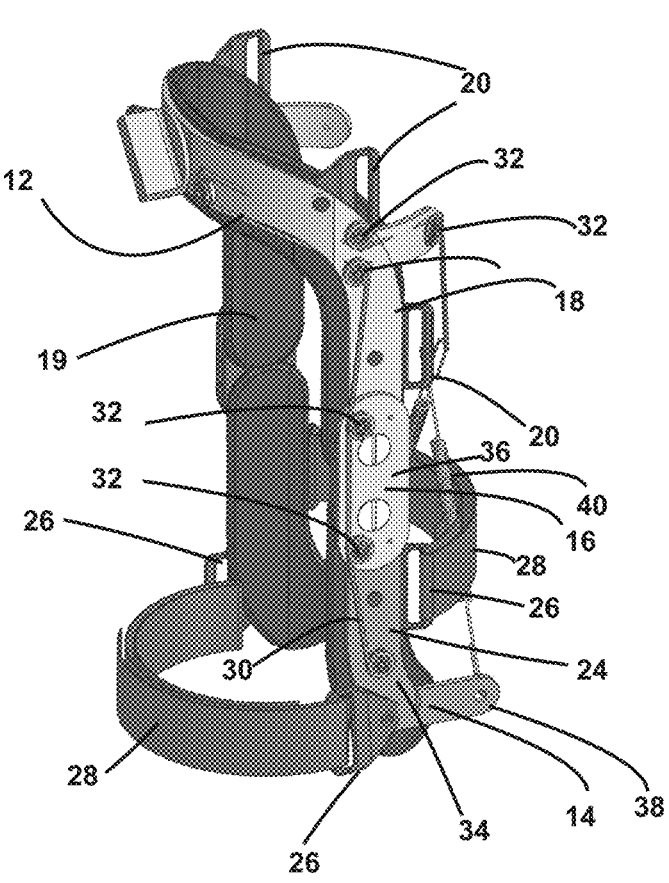
FIGS. 1A-B illustrate one embodiment of the orthosis of the present invention from the front (FIG. 1A) and back (FIG. 1B).
Figure 1B:
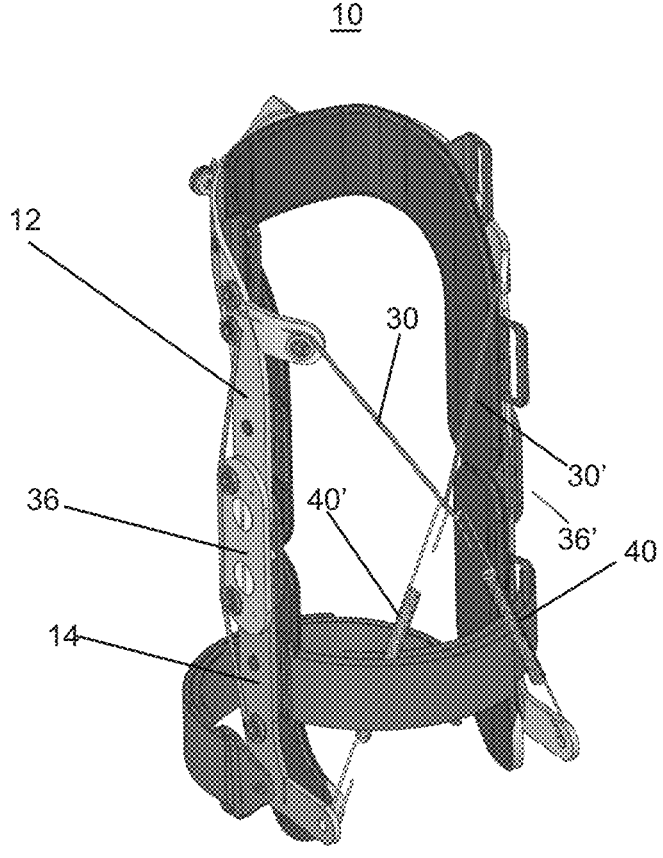

The present invention is of a leg orthosis which can be used for knee conditioning or rehabilitation. Specifically, the present invention can be used to strengthen a leg in order to prevent ACL ruptures or for rehabilitation following ACL rupture repair.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Braces and orthosis for stabilizing and rehabilitating a knee are well known in the art (e.g., Berg company, Asure, MacDavid). Such devices include rigid femur and tibia frames that articulate around the knee and produce a static force that limits tibia anterior translation.

Some devices also use springs in order to enhance extension and to improve the range of motion around the knee.

Although orthotic devices are used by athletes following ACL reconstruction, studies have shown that currently available orthotic devices do not prevent ACL injury and do not reduce the strain on the ligament since they do not prevent tibia translation during high velocity movement such as drop landing or restrict tibia rotation. In addition, these devices are not adjustable to match a subject's joint laxity or movement pattern nor do they monitor the subject load for better load management.

Although orthotic devices fitted with springs can increase the range of motion, they do not enhance stabilization since spring tension does not mimic the balance of muscle force and ligament tension necessary for stabilization.

While reducing the present invention to practice, the present inventor postulated that an orthosis that can provide a desired muscle/ligament tension ratio and mimic a pulling force of an ACL on the tibia can mimic the biomechanics of a knee during standing or locomotion without the significant effects of muscle force that can limit performance while providing maximal comfort for a user.

Thus, according to one aspect of the present invention there is provided an orthosis for treating or rehabilitating a joint injury. The orthosis can be any external appliance that spans a lower or upper extremity joint or joints (e.g., leg orthosis spanning a knee). Examples include foot orthoses, ankle-foot orthoses, knee-ankle-foot orthoses and hip-knee-ankle-foot orthoses. Thus these braces can cover multiple joints in the lower extremity or just a few. The orthosis can be used to prevent injury, to treat arthritic conditions as well as be used for postoperative stabilization in ligamentous reconstruction of a joint such as the knee.

The leg orthosis of the present invention includes a first brace (also referred to herein as 'upper' or 'femoral' brace) attachable to a femoral portion of a leg, a second brace (also referred to herein as 'lower' or 'tibial' brace) attachable to a tibial portion of the leg and an articulation mechanism for enabling articulation of the orthosis.

The leg orthosis of the present invention also includes a force-applying mechanism for applying a pulling force to the second brace in a direction of the first brace. The force-applying mechanism can be positioned near the center of articulation and integrated into the articulation mechanism.

As is further detailed hereinunder, the pulling force applied by the force-applying mechanism can be of variable magnitude throughout flexion (i.e., the force varies in magnitude with an angle of articulation of the leg orthosis).

The magnitude of force applied can be varied with the age of the subject and/or degree of injury. Typically, the force is about 0 at full extension (zero degrees), linearly increases to a maximum of 600-2000 Newtons over a range of 0-15 degrees, remains constant at 15-30 degrees and decreases to a minimum of zero over a range of 30-90 degrees with younger subjects being at the higher end of the force range and older subjects (e.g., over 60) being at the lower end of the force range. As is detailed hereinbelow, the force applying mechanism of the present orthosis includes a mechanism for adjusting the force applied at each of these angle ranges to suit the subject's age or injury.

The force-applying mechanism can be any mechanism that applies a pulling force to the second brace ('tibial' or 'lower' brace) when flexion is above 0 degrees. Examples include a single/multi-lobed cam fitted with a wire or strap interconnecting the first and second braces or a gear mechanism for rotating an element having lobes and throughs that push out and return (radially) a set of pulleys onto which the strap or wire is fitted. In any case, the force-applying mechanism is configured such that rotation around the articulation mechanism produces a pulling force on the second brace towards the first brace only when the angle therebetween is larger than 0 degrees (flexion) with the force increasing with increased flexion to about 15 degrees, remaining constant at 30 degrees and then decreasing to 60 degrees with no force (tension) at 90 degree.

The wire or strap can directly interconnect the first and second braces or through a spring attached to the first or second brace. The spring functions in limiting tibia anterior translation and external rotation of the tibia with respect to the femur.

Referring now to the drawings, FIGS. 1A-3C illustrate a leg orthosis constructed in accordance with the teachings of the present invention. The leg orthosis is suitable for knee stabilization and rehabilitation and is referred to hereinunder as orthosis 10.

Orthosis 10 includes a first brace 12 attached to a second brace 14 via an articulation mechanism 16. First brace 12 includes a rigid frame 18 shaped and sized to be fitted over a femoral (upper) portion of a leg. Frame 18 can be constructed from an alloy or polymer at various sizes to fit various sized femurs. The inner surface of frame 18 can include a cushioning layer 19 (e.g., polymer foam) for comfort. First brace 12 can also include one or more pairs of strap buckles 20 (two pairs shown) for securing frame 18 to the femur using, for example, Velcro straps.

Second brace 14 is constructed similarly to first brace 12 and also includes a rigid frame 24 constructed from an alloy or polymer at various sizes to fit various sized lower legs (tibia). The inner surface of frame 24 can include a cushioning material (e.g., polymer foam) for comfort. Second brace 14 can also include one or more pairs of strap guides 26 (two pairs shown) for securing frame 24 to the tibia using, for example, a Velcro strap 28. In second brace 14, strap guides 26 point in opposite directions (anterior-posterior) in order to stabilize second brace 14 on the tibia.

First brace 12 and second brace 14 also include wire/strap guides 32 (e.g., rollers) for guiding a wire/strap 30 from a first point of attachment 34 at second brace 14 through a force-applying mechanism 36 to first brace 12 and back to a second and (optionally cantilevered) point of attachment 38 at second brace 14. Wire/strap 30 can be attached to second point of attachment 38 through a spring 40 having a spring constant (k) of 150-250 newton per mm (N/mm millimeters). FIG. 1A illustrates force-applying mechanism 36 and related components on the medial side of orthosis 10. It is to be understood that the lateral side can also include a force-applying mechanism 36' and related components including a spring 40' and strap 30' (shown in FIG. 1B) as well as any components described herein with respect to force-applying mechanism 36. Orthosis 10 can include and employ one or both force-applying mechanisms.

Second point of attachment 38 can be cantilevered about 1-10 cm away from second brace 14 in order to apply a pulling force to the front of the tibia and limit anterior translation.

The routing of wire/strap 30 from second brace 14 through first brace 12 and back to second brace 14 is selected so as to transfer force from the lower attachment point (tibial component to the upper femur component.

Articulation mechanism can be a single hinge configuration or a multiple hinge configuration.

Wire/strap 30 can be constructed from a coated steel wire, a Kevlar braid or the like. Wire/strap 30 is substantially non-elastic although configurations having an elastic wire/strap 30 or a wire/strap 30 having an elastic portion (e.g., portion near second point of attachment 38 replacing spring 40 are also envisaged herein.

Figure 2A:
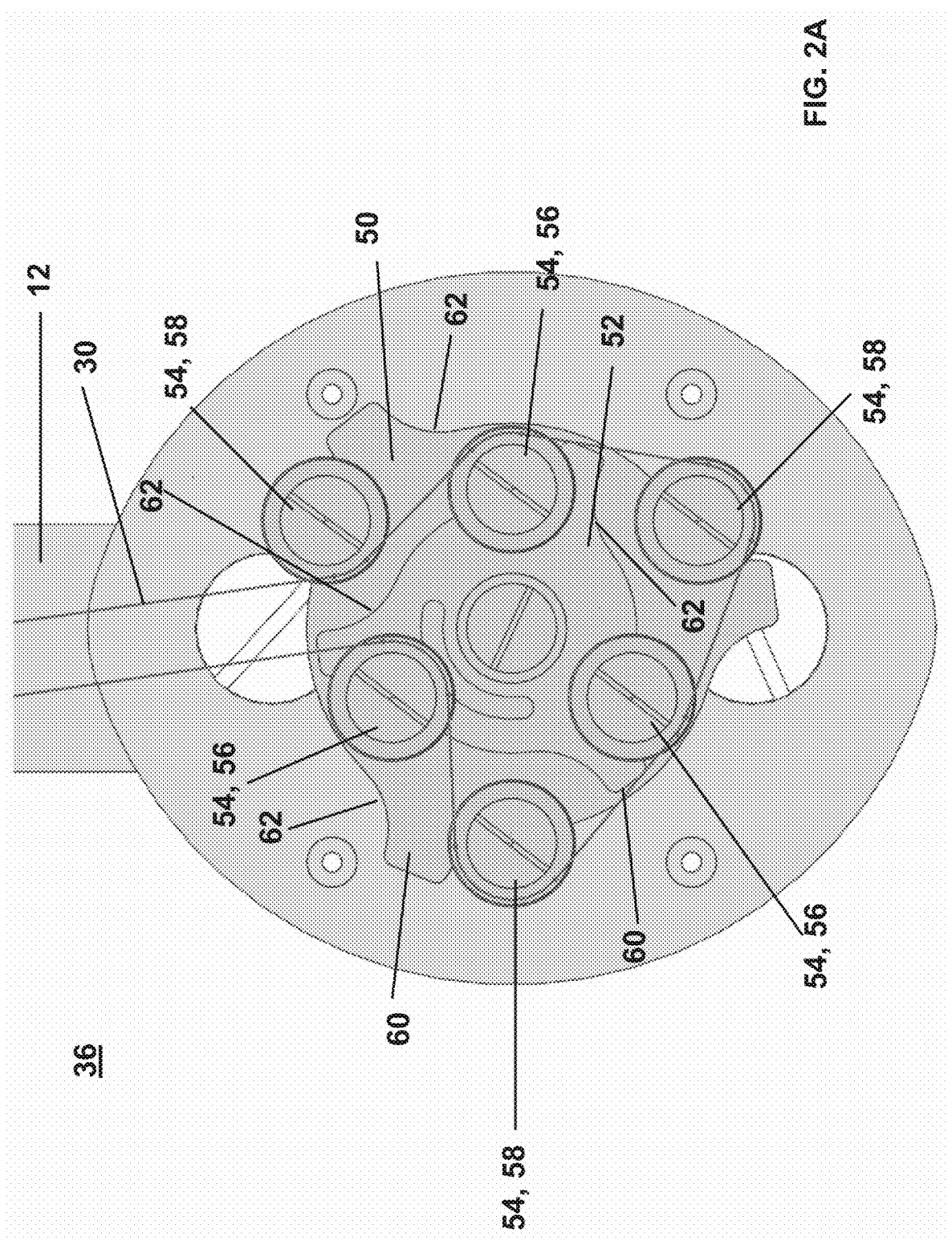
FIGS. 2A-B illustrate an embodiment of a force-applying mechanism of the present orthosis in a low tensioned (FIG. 2A) and high tensioned (FIG. 2B) states.
Figure 2B:
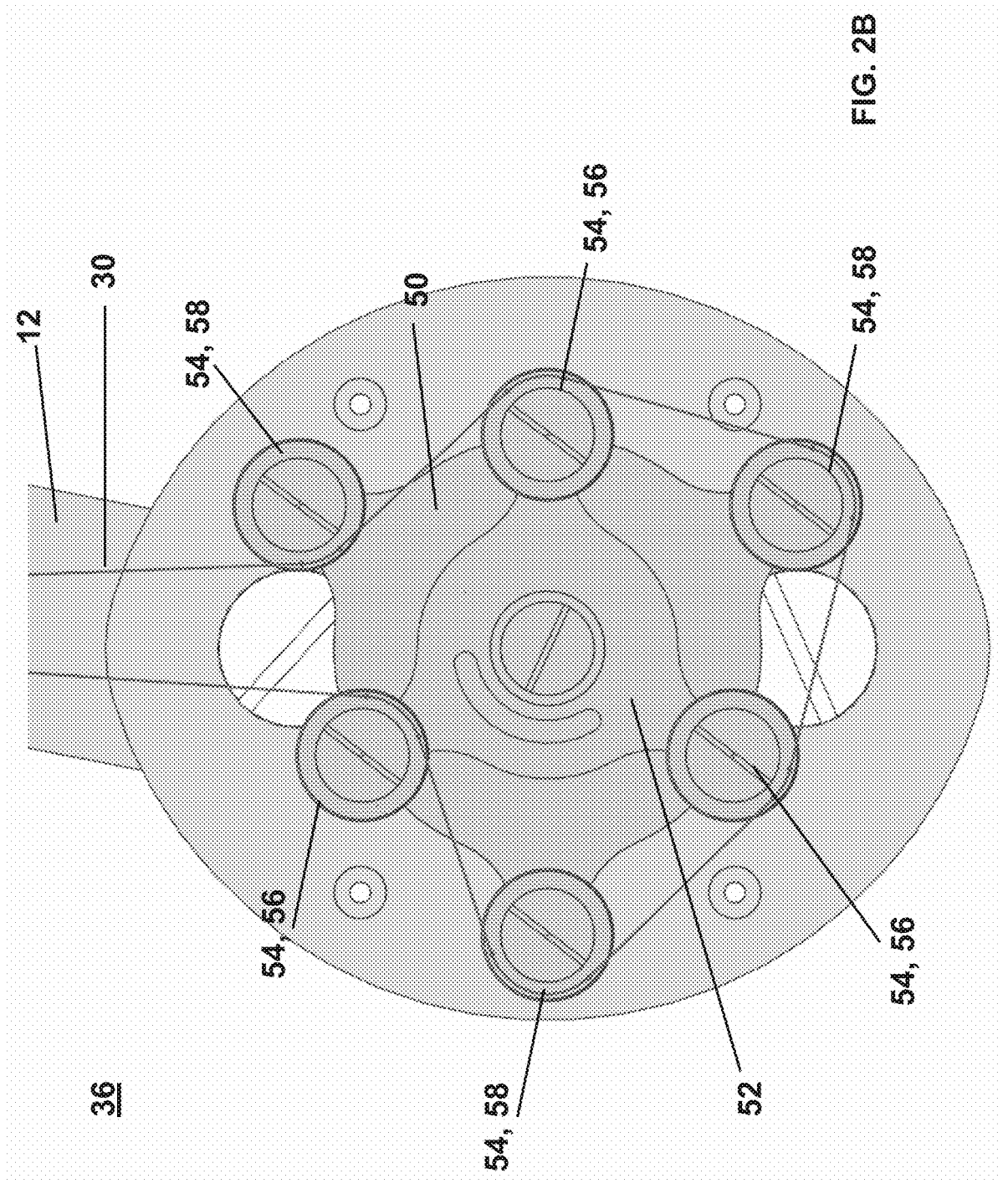

The internals of force-applying mechanism 36 are shown in greater detail in FIGS. 2A-B). In FIG. 2A, force-applying mechanism 36 is shown at 0 degrees of flexion (i.e., no significant tension is applied to wire/strap 30). In FIG. 2B, force-applying mechanism 36 is shown at 30 degrees of flexion (i.e., significant tension is applied to wire/strap 30).

Force-applying mechanism 36 includes a first rotatable element 50 and a second rotatable element 52 and two sets of three pulleys 54, a first set of internal pulleys 56 and a second set of external pulleys 58.

Force-applying mechanism 36 shown in FIGS. 2A-B is integrated into articulation mechanism 16 such that flexion of orthosis 10 operates a set of gears (not shown) that rotates first rotatable element 50 and second rotatable element 52 together in a counterclockwise direction. First set of internal pulleys 56 and second set of external pulleys 58 are arranged around first rotatable element 50 and second rotatable element 52 (respectively). The axles of pulleys 56 and 58 are fitted in slots such that they can move radially in and out as elements 50 and 52 are rotated. Each of elements 50 and 52 includes cams 60 and troughs 62 (three cams and 6 troughs are shown for each element), elements 50 and 52 can be symmetric or cams 60 and troughs 62 can be of varying sizes (in each element and in between elements).

As elements 50 and 52 rotate, cams 60 push pulleys 56 and 58 radially outward thereby tensioning wire/strap 30 while troughs 62 decrease or release tension on wire/strap 30. Thus, movement of elements 50 and 52 through flexion produces variable tension on wire/strap 30 that rises and then fall as flexion progresses up to 90 degrees. At 90 degrees (as with 0 degrees), the tension is about 0 Newtons.

Figure 3A:
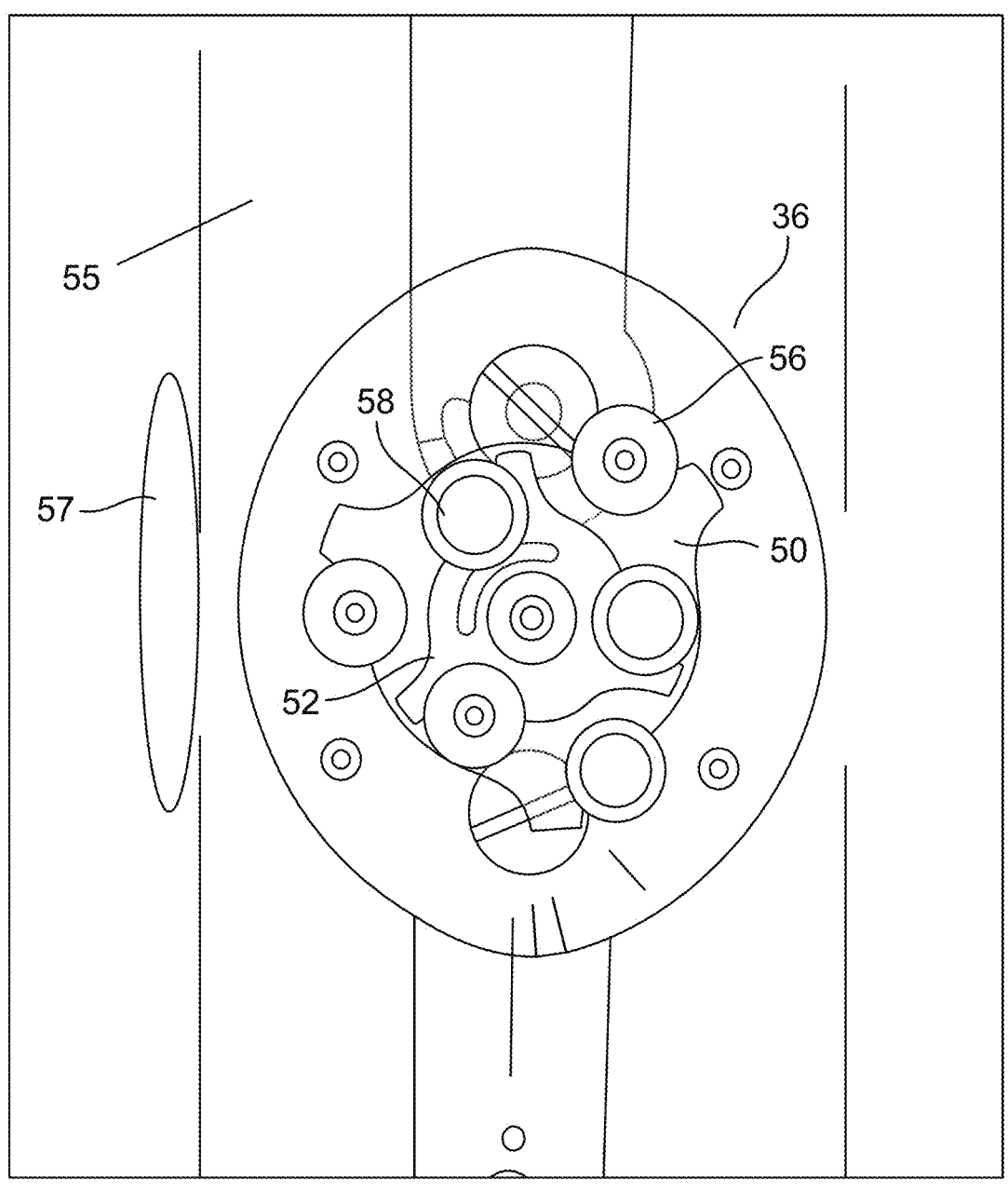
FIGS. 3A-C illustrate the function of the force-applying mechanism of FIGS. 2A-B at three different angles of leg flexion.
Figure 3B:
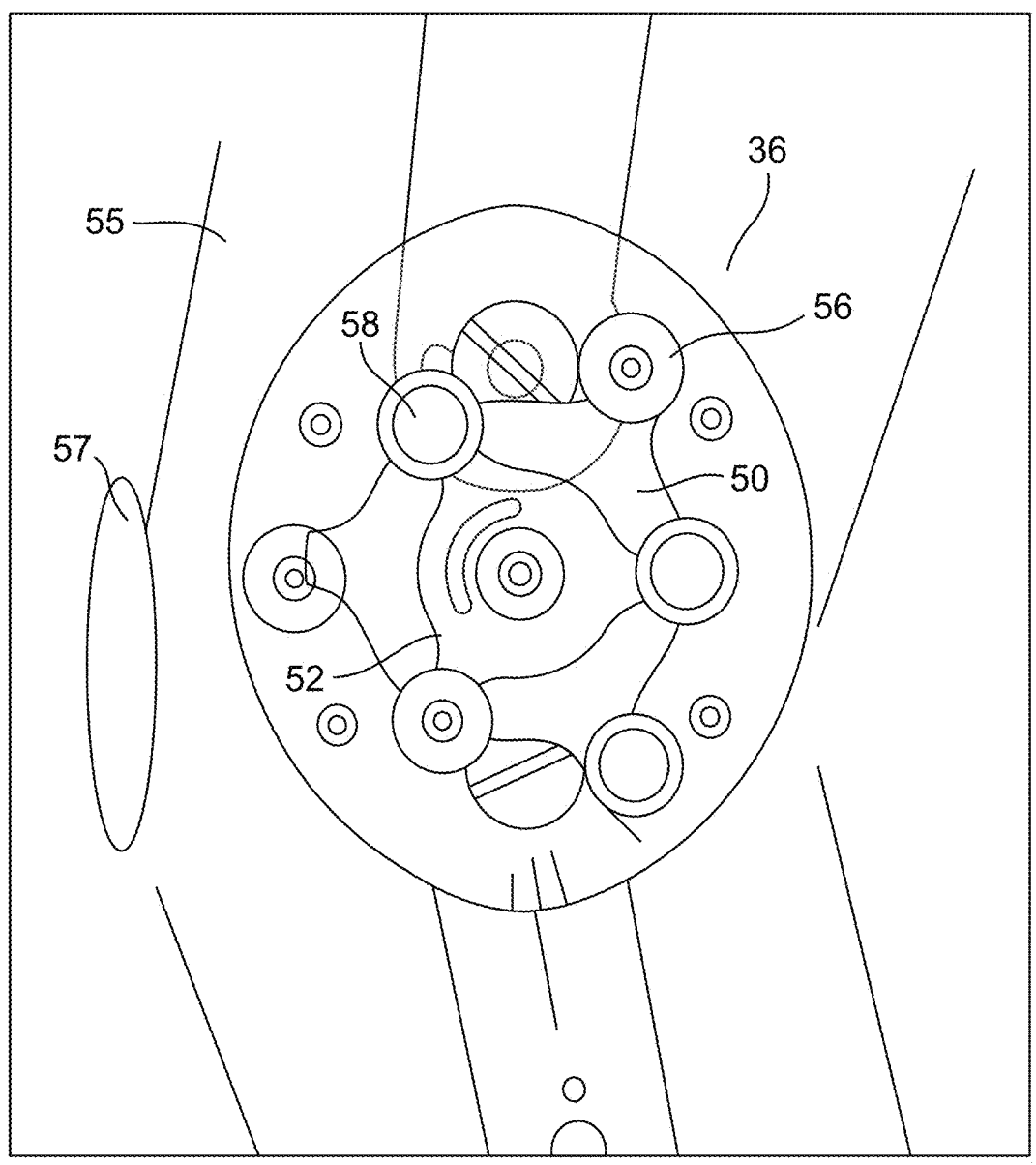
Figure 3C:
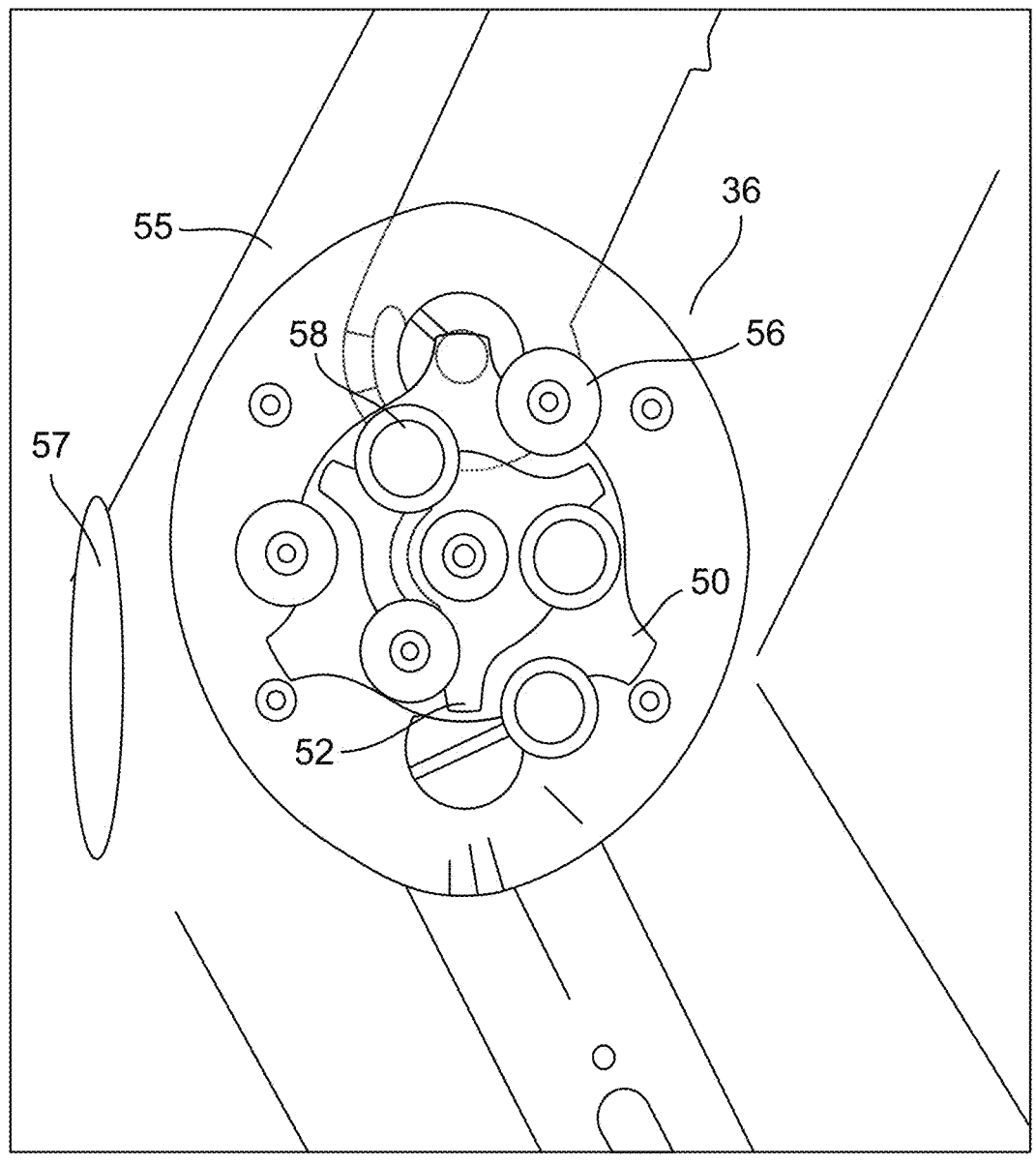

FIGS. 3A-C illustrate the rotational position of elements 50 and 52 and the radial position of pulleys 56 and 58 of force-applying mechanism 36 at 3 stages of leg 55 flexion (0, 15 and 30 degrees respectively). Patella 57 of leg 55 is shown for reference.

To calibrate force-applying mechanism 36 of orthosis 10, tension sensors (and optionally accelerometer) are connected to springs 40 and 40' (accelerometer can be connected to second brace 14 of orthosis 10). Orthosis 10 is worn by a user and cycled through flexion and extension with the sensors connected to a control and data collection unit. During motion, tension data from the sensor is transferred along with velocity (accelerometer) and angle of orthosis 10 to a memory card of the control unit. The information is stored and transferred via Bluetooth or Wi-Fi to a phone application.

The application has three modes: personal data interface, movement monitoring and calibration.

The user data collected from the sensors is analyzed by the application to derive a number of total knee movements, a number of high risk movements, flex angle and rotation at high speed and force.

The velocity of movement (tibial movement during knee movement) is performed by comparing information from the two spring sensors. The load is calculated by comparing spring tensions from the two springs. The spring tension is a sum of anterior translation and rotation—the lateral spring is under tension during medial rotation while the medial spring is relaxed during medial rotation. This calculation can give the net of anterior translation which is an indication of ACL stress. Spring tension can then be set manually or automatically according to this data collected from the user.

The amount of tibia rotation can also be derived from spring tension since tibia rotation causes spring elongation.

During a manual ACL test such as the Lachman test or the Anterior drawer test the end of range of tibial movement (when pulled) provides an indication whether the ACL is intact (firm end of range) or ruptured (soft end of range).

During movement, spring tension can monitor the end of range feel. When movement is performed, if the springs reach maximal length and stop the movement that indicates no stress on the ACL. Tracking a firm end (via spring-attached sensors) at spring maximal length indicates that a load on the ACL and spring should be re-calibrated to add tension.

The information collected with respect to movement and tension can be collected over time (days months) and historical data can be compared to newly obtained data throughout use in order to track treatment and to recalibrate tension if necessary.

Calibration can be performed as follows. A user's personal information such as gender, medical status (post injury, pain), sport type, activity level etc. are entered and the biomechanical characteristics described above are collected during a physical test that includes several stages:

(i) Knee passive function-no initial tension on the springs with the subject lying on the bed wearing the brace and ACL properties are examined as described above. Spring tension can then be increased or decreased according to ACL state as determined from the spring sensors.

(ii) Active calibration-without an initial spring tension the user is asked to perform physical tasks such as two leg squats, one leg squats, drop jump from a high surface and landing on one leg. The application will store the spring tension data (of springs 40 and 40') and will analyze it to provide a recommendation with respect to an initial spring tension that provides maximal support.

As used herein the term "about" refers to +10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

In addition, any priority document(s) of this application is/are hereby incorporated herein by reference in its/their entirety.

8

What is claimed is:

1. A leg orthosis comprising:
(a) a first brace attachable to a femoral portion of a leg;
(b) a second brace attachable to a tibial portion of said leg;
(c) an articulation mechanism for enabling articulation of the leg orthosis; and
(d) a force-applying mechanism for applying a pulling force to said second brace in a direction of said first brace, wherein said pulling force applied by said force-applying mechanism varies with an angle of articulation of the leg orthosis wherein said force-applying mechanism includes a rotatable element for applying a pulling force on a strap or wire interconnecting said first brace and said second brace and pulleys mounted within radially projecting slots for carrying said strap or wire and further wherein said rotatable element includes cams and troughs for moving said pulleys radially in and out as said rotatable element is rotated.

2. The orthosis of claim 1, wherein said pulling force is about 0 Newtons at full extension, linearly increases to a maximum of 600-2000 Newtons over a range of 0-15 degrees and decreases to a minimum of zero Newtons over a range of 30-90 degrees.

3. The orthosis of claim 1, wherein said force-applying mechanism includes two of said rotatable elements and six of said pulleys and further wherein a first rotatable element moves a first set of three pulleys and a second rotatable element moves a second set of three pulleys.

4. The orthosis of claim 1, wherein said strap or wire is connected to said first or said second brace via a spring.

5. The orthosis of claim 1, wherein said force-applying mechanism is integrated into said articulation mechanism.

6. The orthosis of claim 1, wherein said pulling force applied by said force-applying mechanism is configured to mimic a pulling force of an ACL on said tibial portion.

7. The orthosis of claim 2, wherein said force-applying mechanism includes a mechanism for setting said pulling force applied at each degree range.

* * * * *